United States Patent [19]
Diaz et al.

[11] Patent Number: 5,386,442
[45] Date of Patent: Jan. 31, 1995

[54] METHOD AND APPARATUS FOR CONTROLLING THE LOAD ON DOUBLE CANTILEVER BEAM SENSORS

[75] Inventors: Thomas P. Diaz, San Martin, Calif.; Peter L. Andresen; William R. Catlin, both of Schenectady, N.Y.; Gary W. Contreras, San Jose, Calif.; Ronald E. De Lair, Schenectady, N.Y.; William D. Miller, San Jose, Calif.; Harvey D. Solomon, Schenectady, N.Y.; Daniel Weinstein, San Jose, Calif.

[73] Assignee: General Electric Company, San Jose, Calif.

[21] Appl. No.: 83,140

[22] Filed: Jun. 25, 1993

[51] Int. Cl.$^6$ .................................. G21C 17/00
[52] U.S. Cl. ........................... 376/245; 376/247; 376/249
[58] Field of Search .............. 376/247, 249, 245, 255, 376/305, 258, 259; 93/799, 862, 634; 976/DIG. 207, DIG. 210, DIG. 214

[56] References Cited

U.S. PATENT DOCUMENTS

| | | | |
|---|---|---|---|
| 3,303,451 | 2/1967 | Yuan | 338/4 |
| 4,017,819 | 4/1977 | Pien | 338/4 |
| 4,075,884 | 2/1978 | Barker | 73/91 |
| 4,481,826 | 11/1984 | Ingraffea | 73/799 |
| 4,524,624 | 6/1985 | Di Noia et al. | 73/708 |
| 4,677,855 | 7/1987 | Coffin, Jr. et al. | 73/799 |
| 4,711,754 | 12/1987 | Bednar | 376/245 |
| 4,875,170 | 10/1989 | Sakurai et al. | 364/507 |
| 4,895,027 | 1/1990 | Manahan, Sr. | 73/799 |
| 4,908,775 | 3/1990 | Palusamy et al. | 364/508 |
| 4,924,708 | 5/1990 | Solomon et al. | 73/799 |

*Primary Examiner*—Donald P. Walsh
*Assistant Examiner*—Meena Chelliah
*Attorney, Agent, or Firm*—J. S. Beulick

[57] ABSTRACT

An apparatus and a method for measuring and controlling the crack growth rate within a double cantilever beam type test specimen. The arms of the test specimen are fitted with a pressure-actuated bellows to induce a predetermined load and with a sensing assembly to provide feedback on the amount of beam displacement resulting from application of that load. In this manner a loaded test specimen may be remotely mounted and adjusted inside the reactor pressure vessel or piping of a nuclear reactor in order to maintain a stress intensity which is constant or which varies in a predetermined manner for inducing stress corrosion cracking or corrosion fatigue in the specimen.

20 Claims, 2 Drawing Sheets

METHOD AND APPARATUS FOR CONTROLLING THE LOAD ON DOUBLE CANTILEVER BEAM SENSORS

FIELD OF THE INVENTION

This invention is directed to sensors that measure and monitor damage to structural components within aggressive service environments. More particularly, it is directed to double-cantilever beam sensors for measuring crack growth in structural components.

BACKGROUND OF THE INVENTION

Exposing structural material to an aggressive environment under steady or cyclic stress can cause damage in the form of cracking. This result is generally referred to as stress corrosion cracking ("SCC") or corrosion fatigue. For example, metallic alloys used as structural members often operate under sustained or cyclic stress and in high-temperature, oxygenated water, such as that found in boiling water reactors (BWRs), where temperatures and pressures exceed 280° C. and 1000 psi, respectively. The BWR environment may also be radioactive and provide only limited space to accommodate the placement of a sensor to monitor SCC.

Damage in the form of SCC, or other stress/environment induced cracking, is of greater concern to the nuclear industry. The problems which industry faces in attempting to predict the onset of, or susceptibility of particular structural components to SCC under specific operating conditions are set out in U.S. Pat. No. 4,677,855 to Coffin, Jr. et al. and U.S. Pat. No. 4,923,708 to Solomon et al., the disclosures of which are incorporated by reference herein.

Methods for measuring crack growth which require test specimens to be removed from their testing environment have been disclosed over the years. These methods use a variety of monitoring systems including visual and electrical potential (voltage) drop measurements. The electrical potential drop method improved the art by enabling mathematical models to be generated which were effective in monitoring the rate of crack propagation in a specimen. These models are described in detail in the Coffin and Solomon patents.

Material testing for SCC is often carried out using a specimen constructed in a double cantilever beam (DCB) geometry, which has a machined slot at its root notch. The bifurcate specimen is then loaded to force apart the beams of the DCB, e.g., using an electrically nonconductive wedge, thereby inducing crack growth at the machined slot. The rate of crack growth may be monitored and used to assess the aggressiveness of the specimen's environment.

Preferably, the intensity of the applied stress, termed the "stress intensity factor", remains constant at the leading edge of the crack. The rate of crack growth would then be expected to be constant, given an unvarying environment. However, the wedge loading approach results in a nonconstant load as the DCB material creeps and as the DCB material's compliance increases due to a growing crack length. A decreasing stress intensity causes the crack growth rate to slow. Eventually, the stress intensity factor may decrease below the threshold required for SCC. Crack growth will then stop and the sensor will no longer function as an SCC monitor unless additional load is introduced.

One method for applying a constant load to a specimen is to hang an appropriately sized weight from the end of one of the beams while the other beam is captively retained. Here, unlike the wedge loading arrangement, an increase in specimen compliance, resulting from increased crack growth, increases the stress intensity factor. This is not desired since a constant, rather than increasing, stress intensity factor isolates changes in crack growth as being due to changes in the specimen environment.

Generally large testing machines and devices capable of applying loads to DCB specimens have long been known and are in common use. Such machines may involve arms that interlock with the beam components of the DCB specimen and, when energized, move apart, widening the specimen slot. An example of an apparatus with utilizes this method of loading is disclosed in U.S. Pat. No. 4,481,826 to Ingraffea, which discloses the use of expandable jaws driven apart by a threaded knob.

Alternatively, a loading machine may consist of an inflatable pressure bag which, when installed between the beams of a DCB specimen and inflated, tends to widen the specimen slot. This type of apparatus is disclosed in U.S. Pat. No. 4,075,884 to Barker.

However, neither device disclosed by Ingraffea or Barker provides for monitoring the load actually applied to the specimen beams. In addition, these configurations require too much space to be practically employed in BWR applications. Finally, the pressurized bag disclosed by Barker has a nearly infinite compliance and is therefore incapable of being pre-tensioned. Since the specimen loading device of Barker has little inherent spring modulus, it must rely wholly on external fluid pressure to exert any load on the arms of a test specimen.

Thus, there has been a need for a method for applying a constant stress intensity to a remotely mounted DCB specimen. With a constant stress applied, the rate of crack growth can be correlated with the effects of adjusting the specimen's environment.

SUMMARY OF THE INVENTION

The present invention is directed to an improved apparatus and method for controlling the crack growth rate within a DCB type test specimen. This specimen is provided with a pre-formed crack at the root of the notch between its two beams. The DCB specimen is then exposed to an aggressive environment while an adjustable load is applied to its beams sufficient to induce the pre-formed crack to grow. Crack length is monitored, such as by the voltage drop method, and the rate of crack growth is determined.

The DCB geometry may vary in length and cross section depending upon the physical restrictions of a particular application. In the extreme, the invention may also be applied to a short stiff fracture specimen such as a compact tension ("CT") specimen. CT specimens are described in detail in ASTM Standard E 399-83, entitled "Standard Test Method for Plane-Strain Fracture Toughness of Metallic Materials" the disclosure of which is incorporated by reference herein.

In accordance with the invention, the arms of a DCB type test specimen are fitted with a pressure-actuated bellows for inducing a load and a sensing assembly for providing load control feedback. In particular, the load control feedback sensing assembly comprises a proximity device for determining the resulting crack opening displacement. It is also envisioned that a small, compressive load cell may be employed to provide load control feedback. Having measured the crack length and knowing the specimen compliance, i.e., the amount of deflection exhibited by a specimen when subjected to a given load, displacement of the specimen arms and the spring constant of a bellows-type loading mechanism, the stress intensity at the crack tip may be calculated. Pressure applied to the bellows loading mechanism may be adjusted, as necessary, to accommodate for the temperature and/or stress-induced material creep or the reduced loading due to DCB crack growth, thereby allowing a constant stress intensity to be maintained, if desired. Furthermore, the specimen may be preloaded by mechanically compressing the bellows between the specimen arms, thereby utilizing the inherent spring constant of the bellows to provide partial loading to the specimen. The bellows spring constant, as used herein, equals the amount of additional force necessary to deflect the unrestrained, unpressurized bellows an additional unit distance.

During separation of the ends of the DCB sensor beams, the pressurized bellows expands by an amount equal to the relative displacement of the beam ends. As the bellows expands, the spring load exerted by the bellows (which is independent of the gas pressure in the bellows) decreases. Accordingly, to calculate the amount of force being exerted by the pressurized bellows, the decrease in spring load must be taken into account. Thus, unlike the flexible bag disclosed in Barker, the bellows-loaded DCB crack growth sensor of the present invention requires a means for accurately determining the relative displacement of the beam ends, which information enables computation of the variation in spring force due to the bellows.

The measurement and control technique of the invention may be used as a water chemistry check monitor or to assist in determining or estimating the damage caused by aggressive environments on structural components exposed to stress. Sensor crack growth may then be monitored as the chemistry of the environment is altered to determine the effect changing various environmental factors has on SCC.

Alternatively, the apparatus and method of the invention may be employed in materials research to identify and predict the relative susceptibility of various material compositions to SCC under simulated environmental conditions for both BWR and non-BWR applications.

DETAILED DESCRIPTION OF THE PREFERRED EMBODIMENTS

In the course of its general use, a DCB sensor is fitted with a load-inducing assembly and a proximity detector to determine the amount of deflection experienced by the sensor arms as a result of applying a load. The DCB is also fitted with multiple probe contacts for electrically determining the crack length by the voltage drop method as described in detail in the Solomon patent. A desirable constant stress intensity factor and a concomitant rate of crack propagation may be maintained at the root notch of a DCB sensor by controlling the pressurization of a bellows fitted in between the two beams of the sensor while monitoring the resultant beam deflection.

The stress intensity factor at the tip of a sharp crack is dependent upon many variables, including the geometry or configuration of the body of the specimen and the conditions under which it is loaded. A detailed analysis of calculating the stress intensity factor for a specimen having DCB geometry is provided in Stress Analysis of Cracks Handbook by Tada, Paris and Irwin, Dell Research Corporation, Hellertown, Pa. (1973), pp. 29.3 and 29.4. The numerical solution for a specimen's stress intensity factor can be represented by the general formula $K_I =$ (applied stress) $\times$ (crack length)$^{\frac{1}{2}} \times Y$, where Y is a parameter representing the geometry of the crack and the specimen including variables, such as, the width of the body and the distance of the crack from the surface of the specimen.

A more accurate formula for computing the stress intensity (K) for DCB sensors having a constant cross section is provided below:

$K = CF\alpha/(BI)^{0.5}$ (under a constant load)

$K = 3CE\gamma(I/4B)^{0.5}/\alpha^2$ (under wedge load)

where $dC/d\alpha$ for plane stress or $1/(1-v^2)^{0.5}$ for plane strain; F is the applied force; G is the crack length; B is the crack width; I is the moment of inertia of the beam cross section about the neutral axis of the beam (assuming both beams have identical cross sections); and $\delta$ is the crack opening displacement (COD).

For DCBs having varying cross sections, the following formulae may be used to determine the required stress intensity to induce crack growth:

$G = F^2(dC/d\alpha/(2B)$ $G = K^2(1-v^2)/E$ where $dC/d\alpha$ is the derivative of DCB compliance with respect to crack length; E is the modulus of elasticity; and G is the energy release rate. Solving for K:

$K = F(E(dC/d\alpha)/[2B(1-v^2)])^{0.5}$

Figure 1:
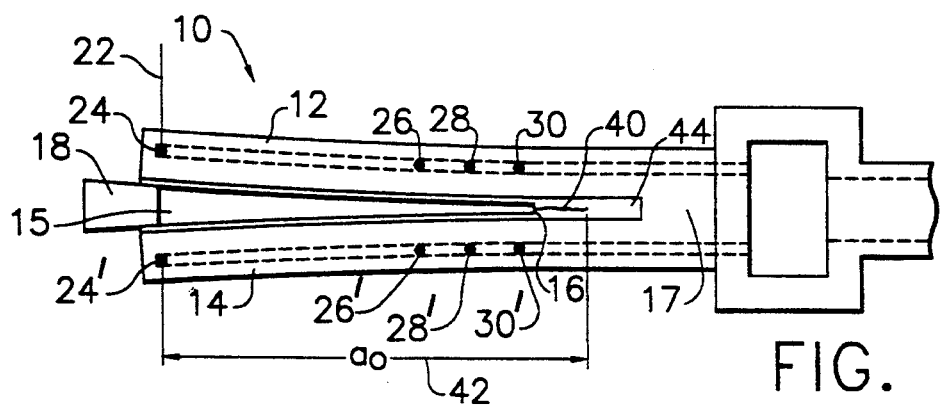
FIG. 1 is a partial elevational view of a conventional DCB crack growth sensor.

Looking to FIG. 1, a conventional configuration for a sensor having a DCB geometry is revealed generally at 10. This compact geometry has been observed to provide high flexibility and sensitivity for measuring SCC. With the DCB geometry, two parallel beams 12 and 14 are joined at one end of a specimen body 17 and separated at the other. This separation is defined by a slot or deep notch 15. This slot 15, which extends to a base 16, is referred to as the "notch root". A pre-formed crack 40 preferably is positioned at the notch root 16, centrally or symmetrically located intermediate beams 12 and 14.

The effective crack length, initially identified as $\alpha_o$, is established by beams 12 and 14 and may be determined by voltage drop methods. The relatively long length of the sensor beams 12 and 14 permits a threshold crack tip stress intensity to be obtained at lower load levels. In one prior art approach shown in FIG. 1, loads sufficient to induce crack growth are obtained by placing a wedge 18 between the two beams 12 and 14 of the sensor. This wedge-loaded approach, however, lacks the advantage of being remotely controllable to provide a constant or other predetermined stress intensity factor.

In accordance with the present invention, sensor 10, having a pre-formed crack 40, may be remotely controlled when placed in an aggressive environment to monitor water chemistry or to conduct material stress tests. The term "aggressive environment" refers to those operative environments that attack the material from which sensor 10 is made with sufficient magnitude to promote crack growth beyond the pre-formed crack 40, i.e., to induce SCC and/or crack growth by corrosion fatigue. To assess the actual or potential damage to a structural component, sensor 10 is typically placed within the same operating environment as the structural component. Sensor 10 then experiences the same changing environmental conditions, such as increased temperatures and changes in chemical balances (e.g., excess $O_2$ content in the water) as the structural component of interest.

Figure 2:
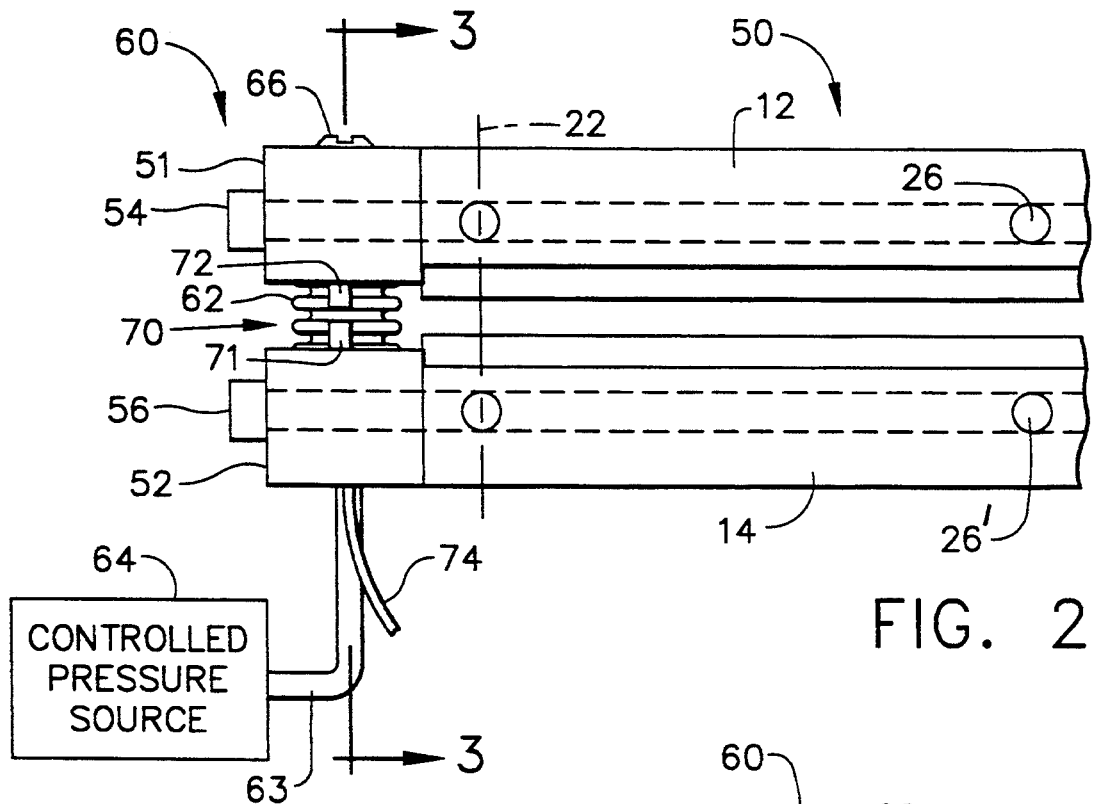
FIG. 2 is a partial elevational view of a DCB crack growth sensor fitted with a bellows loading device and displacement sensor in accordance with a preferred embodiment of the invention.
Figure 3:
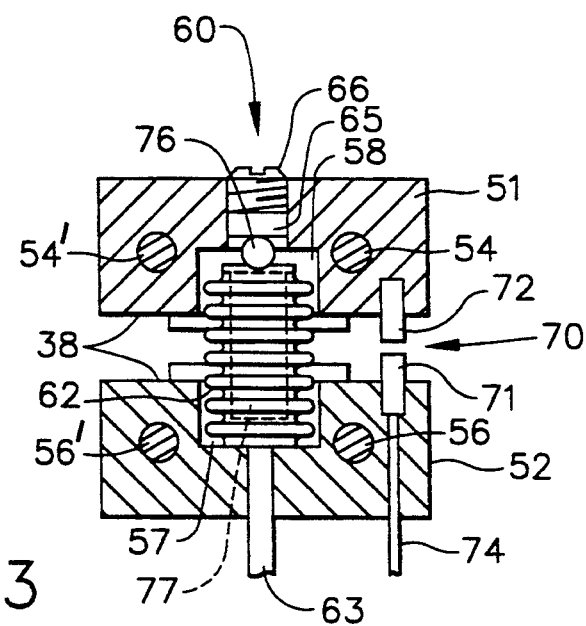
FIG. 3 is a sectional view taken along section line 3—3 shown in FIG. 2.

Referring now to FIGS. 2 and 3, an improved DCB sensor is represented generally at 50. For purposes of clarity, components of sensor 50 which are common with those of sensor 10 of FIG. 1 are identified by the same numerals. Upper and lower mounting blocks 51 and 52 are secured to the ends of respective beams 12 and 14 with corresponding upper and lower retaining bolts 54, 54' and 56, 56', although other techniques for securing the mounting blocks, such as welding, may also be used.

Mounting blocks 51 and 52 serve to retain the transfer load forces generated by a bellows 62 mounted between them. Alternatively, cavities for mounting bellows loading assembly 60 may be machined directly into the ends of arms 12 and 14. This mounting arrangement is shown in FIG. 3. The lower end of bellows 62 is positioned in abutment against the lower internal surface of a cavity 57 formed within block 52. From cavity 57 the bellows extends to a closed top surface which is located within an upper cavity 58 formed within block 51. Clearance between the outer diameter of bellows 62 and the inner walls of mounting block cavities 57 and 58 should be sufficient to allow actuation of bellows 62 without contact with the cavity inner wall surfaces. This is desirable to not only assure electrical isolation but also to avoid abrasive wear of the bellows 62 which may lead to its rupture. Force transfer connection with block 51 from the top of bellows 62 is through a point contact provided by the spherical surface of an intermediate loading ball 76. Ball 76, in turn, provides a self-aligning point contact with block 51 through the lower surface of a set screw 66. Set screw 66 is seen to be threadably engaged within block 51 and extending into cavity 58.

Bellows 62 may be constructed of fully annealed Inconel TM 718 type metal alloy such as manufactured by Mini-Flex Corporation of Ventura, Calif. as part number I-718-320-80-650M. Inconel TM 718 alloy has been shown to be preferable for constructing the bellows for in-core DCB sensors since this material has been demonstrated to have a 3 to 4 year SCC initiation time in aggressive neutron environments such as a BWR. Since the life expectancy of a stress-corrosion sensor is only one to two years, the Inconel TM 718 material will not undergo appreciable stress corrosion during its useful life. It is also preferable to heat treat bellows 62 prior to use as the instant loading mechanism. While a variety of approaches will occur to those skilled in the art to heat treat bellows 62, one heat treating sequence provides for such treatment to occur at 718° C. for 8 hr and then at 621° C. for 8 hr. One configuration of bellows which was fabricated for loading a DCB sensor 50 has a spring constant of around 650 lbs/in., although bellows having other spring constants may be employed. A minimum spring constant of 200 lbs/in. is desirable in order to use bellows 62 to partially preload sensor 50.

When internal pressure is applied to the unreinforced bellows 62, a condition known as "squirming" may occur. Squirming may manifest itself as a shift or rotation of the plane of one or more bellows convolutions such that the plane of these convolutions is no longer perpendicular to the axis of the bellows. Squirming is detrimental to bellows performance in that it can greatly reduce both fatigue life and pressure capacity. Internal to bellows 62 and extending from one end is a mandrel 77 which forms one base of the bellows, as shown in FIG. 1. The mandrel is preferably solid and made of the same material as bellows 62. The diameter of that portion of the mandrel extending through the bellows is slightly less than the inside wall of the convoluted section of the bellows. As such, the mandrel 77 acts as an internal guide to restrict the bellows 62 from squirming under high pressure, thus enabling use of higher bellows pressures. The length of the mandrel internal extension is approximately equal to the length of the bellows minus the recommended maximum allowable compressive deflection of bellows 62. In this manner, the end of the mandrel 77 serves as a stop to prevent over-compression of the bellows 62 during mechanical preloading of the DCB sensor 50 via set screw 66. A load cell 65 is shown positioned intermediate set screw 66 and loading ball 76. The output of load cell 65 may be used to directly measure the load being imparted to sensor 50 by bellows 62. The load cell may be of the type manufactured by A. L. Design, Inc., model number ALD-Mini-T, which has been determined to be suitable for high-temperature (550° F.) applications. For in-core BWR applications, consideration should also be given to whether the selected load cell construction can withstand an irradiated environment.

To assure necessary electrical isolation between blocks 51 and 52 in conjunction with the mounting of bellows 62, the surfaces of cavities 57 and 58 may be coated with a non-conductive material. Additionally, ball 76 is formed of non-conductive material such as a ceramic exhibiting low compliance, i.e., little or no deflection under normal loading. Also, the ball should be constructed from a material having a small coefficient of expansion. This helps prevent the ball 76 from influencing the load on the sensor 50 and the concomitant stress intensity factor at the crack tip 44 under changing temperature conditions.

The ball contacting surfaces of bellows 62, preferably the base of mandrel 77, and set screw 66 may be constructed with hemispherical depressions in their respective centers. In this respect, when operatively coupled between the bellows and set screw, ball 76 will serve as a load centering mechanism to help maintain the load exerted by the bellows normal, i.e., perpendicular, to the surface of the pre-formed crack 40.

The material utilized for the ball 76 should be resistant to the aggressive environment in which sensor 50 is placed. As an alternative to the spherical geometry of ball 76, flat upright insulating disks (not shown) may also be used. The main design consideration is that a stiff, electrically insulating component be placed along the load transfer line of bellows 62.

Porting is provided through the lower mounting block 52 to permit access by the pressurizing fluid to the lower end of bellows 62. In this regard, a pressure tube 63 extends from bellows 62, through block 52 and to a controlled pressure source 64 (see FIG. 2). Both mounting blocks 51 and 52 are preferably constructed of material having the same coefficient of expansion as the body of the sensor 50 so that changing temperatures will not cause inaccuracy in the measured deflections of beams 12 and 14. When so configured and attached to the ends of beams 12 and 14, the assembly including mounting blocks 51 and 52 is effective for captively retaining bellows 62 in an orientation perpendicular to the plane of pre-formed crack 40.

Returning to FIG. 2, controlled pressure source 64 may supply either pneumatic or hydraulic pressure to bellows 62. It may be preferable to use an inert gas or water when operating the sensor 50 in certain applications to avoid contamination or adverse chemical reactions with the environment in which it is operating in the event of leakage. Further, in nuclear reactor applications, the inlet tube 63 preferably is nearly capillary sized. In this respect, should the tube 63 rupture within the core of a reactor, very little volume of outside air or other pressurizing fluid would be introduced into the reactor. The small size of the tubing tends to prevent it from imposing a moment on the sensor 50. Inlet tube 63 should be constructed of a material which resists SCC in the aggressive environment of a BWR.

A displacement sensor assembly 70 is coupled into the mutually inwardly facing surfaces of upper and lower mounting blocks 51 and 52. Assembly 70 includes a detector 71 and a target 72 for measuring the displacement between beams 12 and 14. Detector 71 may be of a conventional type, such as an eddy current sensor or Hall effect type sensor having an analog voltage output proportional to the distance between sensor 71 and target 72. Such analog sensors provide a continuous voltage output which increases with a strong magnetic field and decreases with a weak magnetic field. Therefore, the voltage output of the displacement assembly 50 will increase as displacement sensor 71 approaches magnetic target 72.

Alternatively, assembly 70 can comprise a laser proximity meter including a laser beam source and detector on one beam and a mirror on the opposing beam, the distance separating the beams being determined by the time of travel of the transmitted and reflected beam.

For BWR or similar applications the sensor assembly 70 must be capable of operating in high-temperature environments having an upper range of 250°–300° C. Also care should be taken to select a displacement sensor assembly 70 having suitable sensitivity and resolution for the total range of bellows displacement.

The displacement sensor output signal is conveyed by wiring or lead 74 extending to the displacement sensor assembly 70. In the preferred embodiment, wiring 74 is shown to be external to the mounting block 52. Alternatively, it may be expedient to route the wiring to the displacement sensor 71 through the beam 14 via an internal wiring channel.

In operation, the stress intensity factor required to induce a desired rate of stress-related crack growth in a specimen is first determined. In this regard, the above-noted formulae for computing the stress intensity factor $K_I$ may be utilized. The applied stress is a function of the amount of deflection in the beams, given a determinable beam length and a known compliance for the specimen material.

Once beam deflection for a required stress intensity is determined, sensor 50 may be preloaded. Preloading allows greater extension of the bellows 62 by utilizing both the compressive and tensile deflection ranges. Preloading is accomplished by mechanically compressing bellows 62 using set screw 66 while monitoring the output of displacement sensor assembly 70. Set screw 66 is tightened until the previously computed beam displacement is achieved. If the DCB is preloaded to some displacement less than that required to achieve SCC, fluid pressure from a controlled pressure source 64 may be applied to the bellows 62 during operation. The amount of pressure to apply to the bellows 62 to achieve a selected displacement may be calculated using the following formula:

$$F_p - F_{DCB} - F_b = 0$$

$$(P_b - p_v)A - x_{DCB}k_{DCB} - x_b k_b = 0$$

where $F_p$, $F_{DCB}$ and $F_b$ are the forces exerted by the pressurizing fluid, the double cantilever beams and the bellows, respectively; $P_b$ and $P_v$ are the pressure in the bellows and in the reactor vessel, respectively; $x_{DCB}$ and $x_b$ are the displacements in the tensile direction of the double cantilever beams and the bellows, respectively; $k_{DCB}$ and $k_b$ are the spring constants of the double cantilever beams and the bellows, respectively; and A is the effective area of the bellows. It is assumed that the pressurizing fluid is incompressible, no creep occurs the DCB or bellows and no leaks occur in either the bellows or associated tubing.

Assuming that the bellows is not compressed initially, i.e., no preload, then $X_{DCB} = x_b$. Combining equations and solving for the bellows pressure yields:

$$p_b = x_{DCB}(k_{DCB} + k_b)/A + p_v$$

While the pressure required to achieve a certain displacement may be calculated, monitoring the actual deflection of beams 12 and 14 provides a positive feedback of the amount of applied load. The procedure of pressurizing bellows 62 to its initial stress point may be performed prior to installing sensor 50 into the core of the BWR. This may be desirable in order that any incipient leaks or other pressure-related defects will be detected prior to introducing the sensor 50 into the nuclear environment.

Once the sensor 50 is positioned in situ within a BWR, the rate of SCC is determined using conventional methods, such as described in the Coffin and Solomon patents. As the length of the crack grows, the amount of load supplied, i.e., the pressure supplied to bellows 62, is adjusted in order to achieve a predetermined stress intensity at the tip of the growing crack. By continually monitoring crack length and making corresponding adjustments in the bellows-applied load, a desired constant or variable stress intensity at the crack tip may be maintained.

Figure 4:
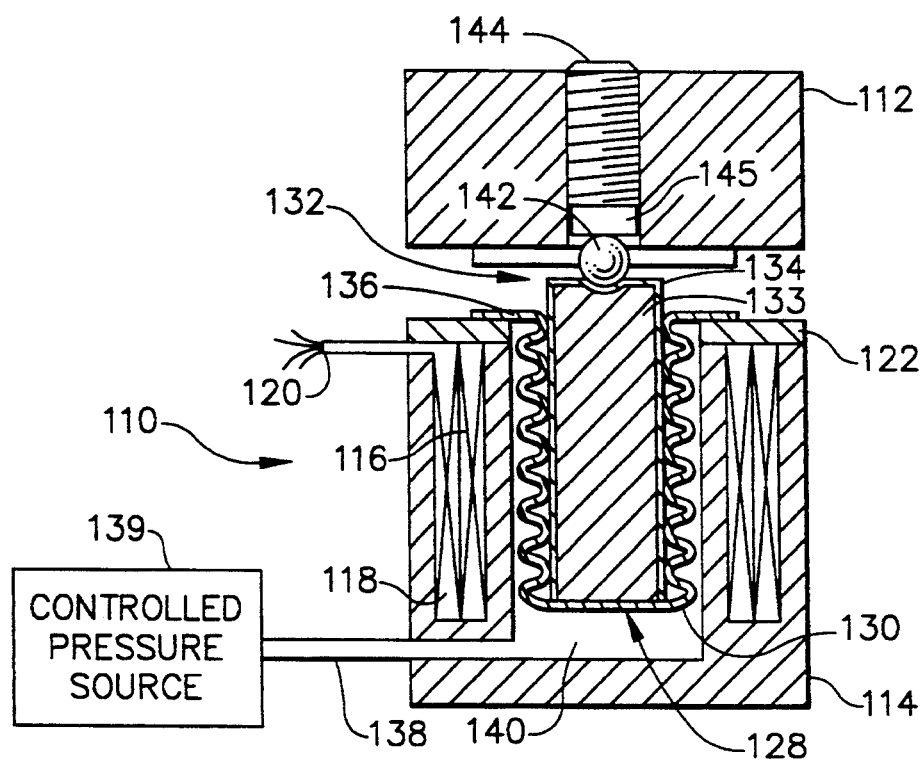
FIG. 4 is a sectional view of a bellows loading device and a linear voltage displacement sensor in accordance with another preferred embodiment of the invention.

Turning to FIG. 4, another embodiment of a sensor according to the instant invention is shown as a cross section taken through its mounting blocks. This embodiment uses an integrated bellows and linear voltage displacement transducer ("LVDT") for both loading and measuring the displacement of the beams of the sensor. A bellows loading and displacement sensor assembly 110 may be substituted for the bellows and displacement sensor assembly 60 shown in FIGS. 2 and 3.

LVDT sensor assembly 110 comprises a housing 114 which may, for example, be constructed of a non-magnetic alloy such as Inconel TM. This type of material offers the advantages of being adaptable for use in an aggressive environment as well as not being susceptible to retaining residual magnetism, which may adversely affect the operation of the LVDT sensor. The housing 114 is generally cylindrical and adapted to be affixed to one beam of a DCB sensor (not shown). Located within the housing 114 and encircling bellows assembly 130 is a primary winding 116 of the LVDT sensor 110. Surrounding primary winding 116 is a secondary winding 118, both windings being operationally coupled to external measurement instruments (not shown) via electrical leads 120. Primary and secondary windings 116 and 118 are constructed in a conventional manner, the windings being electrically isolated from one another and from the housing 114 which supports them. The windings must be precisely wound of a wire gage fine enough to achieve adequate resolution over a typical distance of travel by the core assembly 132. It is preferred that the windings be physically isolated from the environment by a sealant such as gasketing, encapsulation or suitable potting material. Housing 114 additionally may be fitted with a cap 122 to secure the windings within the housing and to provide a base for connecting a bellows.

Located within the housing 114 is a chamber 140 which is appropriately sized for receiving a bellows assembly 128. This sizing provides containment while spacing the surface of bellows component 130 from the inside walls of chamber 140. Bellows component 130 may be constructed of Inconel TM material which has been annealed and heat treated. Bellows assembly 128 further includes a core assembly 132 which is centered within and affixed to the inside capped end of bellows 130. Core assembly 132 is composed of a ferric core 133 which has been covered with a jacket 134 of stainless steel or other relatively non-corrosive material. Alternatively, ferric core 133 may be electroplated with a non-corrosive material, such as gold. It is preferable that the unattached end of core 132 be cupped in its center corresponding to the shape of an insulative force transfer member such as ball 142. For reasons previously described in conjunction with the bellows loading configurations of FIGS. 2 and 3, this spherical or ball configuration assists in maintaining alignment between housing 114 and upper mounting block 112 and in properly directing the load provided by bellows assembly 128, although an insulating disk (not shown) may be substituted or otherwise used in conjunction with ball 142. A load cell 145 is positioned intermediate set screw 144 and loading ball 142. The output of load cell 145 is used to provide load control feedback by determining the amount of load being imparted to sensor 110 by bellows 130.

Bellows assembly 128 is centered within chamber 140 and is affixed to housing cap 122 by circumferentially attaching flange 136 to the face of housing 114 in the area surrounding the circular opening of annular chamber 140. Conventional methods may be employed to secure bellows flange 136 to the housing 114, such as by welding. Bellows flange 136 is affixed to the housing cap 122 in such a manner as to provide a seal between chamber 140 and the environment. If a separate cap is not employed to seal the windings from the environment, the bellows flange 136 may be bonded directly to the body of the housing 114. It is important that the seal be capable of withstanding pressures in chamber 140 in the 2,000 to 6,000 psi range.

Pneumatic or other suitable fluid pressure is introduced to chamber 140 from a pressure inlet tube 138. Tube 138, in turn, is connectable to a controlled pressure source 139. Mounting block 112 is affixed to one beam of the DCB sensor (not shown) in a conventional manner, such as by welding or by bolts (not shown). The block has a threaded shaft for retaining a set screw 144 which is adjustable for urging ball 142 into compressive contact with core assembly 132. Additional methods of distending or clamping the bellows may be employed to preload the specimen that do not involve a set screw.

In operation, primary winding 116 of LVDT assembly 110 is supplied with a voltage from an external source via leads 120 while the secondary windings are monitored by external measuring equipment also connected to the windings by leads 120. The beams (not shown) of the DCB sensor are initially preloaded by adjusting set screw 144. External fluid pressure is supplied to the LVDT sensor assembly from inlet tube 138. As it is desired to remotely adjust the load applied to the DCB sensor, pressure is either increased or decreased via inlet tube 138 to chamber 140, which tends to compress or relax bellows 130. As bellows 130 moves, the changing orientation of ferric core 133 with respect to primary and secondary windings 116 and 118 causes a change in voltage occurring at secondary winding 118. This voltage alteration is linearly proportional to the change in position of the ferric core 133. As such, the LVDT sensor 110 provides a measurement of displacement of the double cantilever beams to which it is coupled.

Figure 5:
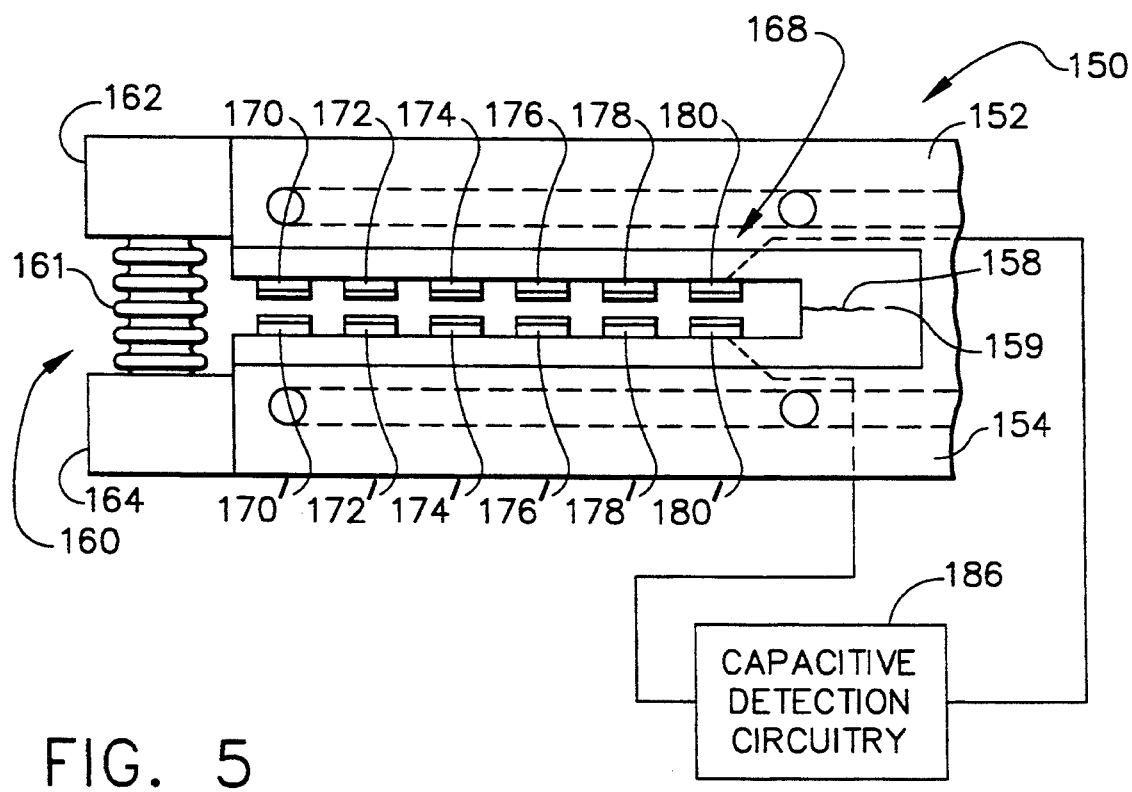
FIG. 5 is a partial elevational view of a bellows-loaded DCB sensor fitted with a plurality of capacitive displacement sensors in accordance with yet another preferred embodiment of the invention.

Turning to FIG. 5, an embodiment of a DCB sensor which utilizes a capacitance extensometer 150 to determine the displacement between the sensor beams is shown in partial elevation. Mounted on the mutually inwardly facing surfaces of beams 152 and 154 are capacitive electrode assemblies formed of oppositely disposed paired components 170, 170' through 180, 180'. Each capacitive component forms one generally parallel plate of a capacitor and consists of a metallic disk which is insulated from the beams of the DCB sensor 150 by an insulating material, such as a ceramic. For BWR applications, the material chosen for the metallic electrode should be suitable for withstanding aggressive environments. The environmental fluid in which the DCB operates provides the dielectric for the capacitor structures, and may be either a liquid or a gas. Structured as metal disks, each capacitive component 170, 170' through 180, 180' is connected to a lead which is routed through respective channels 194 and 194' formed within beams 152 and 154 to external measurement circuitry (not shown). When the DCB sensor 150 is in an unloaded condition, the parallel facing surfaces of the capacitive components 170 and 170' are, for example, spaced apart about 0.100'. Such spacing of the components may need to be adjusted depending upon the dielectric constant of the fluid in which sensor 150 is to operate. When a load is applied by a bellows 161 mounted between mounting blocks 162 and 164 in the manner of FIGS. 2 and 3, the spacing between the facing components typically is about 0.125", depending upon the distance between the crack tip 159 of premachined crack 158 and the respective pair of electrodes.

In this embodiment, it is preferable that the paired capacitor assemblies 170, 170' through 180, 180' be uniformly distributed along the length of beams 152 and 154. Fluid pressure is applied to the bellows 161 from a controlled pressure source (not shown), thereby forcing the beams 152 and 154 to deflect. As the beams deflect, the capacitances of the pairs of capacitive electrodes located on the beams vary with the amount of deflection occurring at each respective pair. Determination of the capacitance values for the pairs is accomplished through use of circuitry, shown generally at 186, operatively coupled to the capacitive pairs. Applying conventional beam theory, i.e., the beam curvature being a function of the applied load, the amount of load being applied to the beams of the sensor 150 may be calculated. A determination of the applied load takes into account the crack length, which, as previously disclosed, can be calculated by the potential drop method using techniques disclosed in the Coffin and Solomon patents. Such determination additionally considers the value of the compliance for the material which comprises the body of the sensor 150, and the curvature of the beams 152 and 154 as determined by plotting the various displacement values acquired at spaced capacitive assemblies 170, 170' to 180, 180'.

The displacement of the arms of the sensor can also be measured by placing the capacitance measuring system within the bellows. One plate would be attached to one face of the bellows and the other to the other face of the bellows. Each plate must be electrically isolated from the bellows and each other. While this embodiment lacks the ability to determine the specimen compliance through the relative displacement at different positions along the sensor arms, it has the advantage of being isolated from the general environment in which the sensor operates. It sees only the environment of the inside of the bellows, which can be kept suitably nonconductive so as not to reduce the sensitivity of the capacitance measurement.

For the purpose of discussing the method of operating the bellows-loaded DCB stress sensor in accordance with the invention, the embodiment shown in FIGS. 2 and 3 shall serve as an example, it being understood that the same operation is generally applicable to each of the embodiments of the invention disclosed in FIGS. 4 and 5, as well as various other sensor geometries, including CT specimens. A test specimen is prepared to serve as a DCB type sensor as is disclosed in the Coffin and Solomon patents. This includes fitting the beams 12 and 14 of the sensor with voltage contacts 24 and 24' and probe contacts 26–30 and 26'–30' for determining crack length $a_0$ by the potential drop method. A suitably sized bellows 62 is mounted at the end of the sensor beams between two mounting blocks 51 and 52. The mounting blocks may also retain a displacement sensor assembly 70 to monitor the displacement between beams 12 and 14, adjusted for load line 22. The bellows is positioned such that its associated pressure inlet tube 63 protrudes from one end of the lower mounting block 52. The pressure inlet tube is operationally coupled to a controlled pressure source 64 for pressurizing bellows 62. An insulating member 76, preferably having a ball shape, is placed in the threaded hole located on top of the upper mounting block so that it rests on top of the end of the bellows 62 opposite the pressure inlet tube 63, preferably in a fabricated depression in the center of the bellows. A set screw 66, also fabricated with a cupped depression in the ball-contacting end, is inserted into the threaded mounting block and is adjusted until it is brought into compressing contact with the ball 76. A reading is taken from displacement sensor 71 to determine the displacement for the unloaded beams. As an alternative to calculating the amount of load being applied by measuring displacement of beams 12 and 14, the magnitude of the load being applied by the bellows 62 may be measured directly by a load cell 65 placed intermediate the bellows and the set screw 66 retained in mounting block 51.

As previously discussed, the bellows has a limited maximum deflection and requires significant pressure to achieve this maximum. In order to get the maximum load potential from the bellows 62, the set screw 66 is used to mechanically compress the bellows. The spring constant of the compressed bellows returns a force back against the mounting block, thereby urging the sensor beams apart. This allows a load to be induced from an unpressurized bellows. As the DCB sensor 50 is preloaded, the displacement of beams 12 and 14 is monitored, and taking into account the crack length, a preselected stress intensity factor value is approached. If the desired stress intensity is not fully achieved by mechanical preloading, during operation bellows 62 is additionally pressurized via controlled pressure source 64. The amount of pressure to be applied may be calculated given the compliance of sensor 50 and the bellows spring constant. The amount of pressure applied to the bellows is preferably monitored by pressure transducers (not shown) operatively coupled to the source of supply 64 and confirmed by the resulting beam displacement as determined by displacement sensor assembly 70. In this manner a constant stress intensity at the crack tip of the sensor may be maintained by decreasing the source pressure as the crack length increases.

In some cases it may be desirable to study the crack growth in a specimen as a function of varying applied stress intensity. Under these circumstances the stress intensities applied to a test specimen may be systematically increased while observing the rate of crack growth in the specimen and the resultant crack growth recorded. Also, for some material types, such as low alloy steel, it may be necessary to cycle the applied loading in order to induce SCC and/or corrosion fatigue cracking. In this regard the invention may be employed to effectively cycle the load between predetermined mined stress intensity limits.

The foregoing preferred embodiments have been disclosed for the purpose of illustration only. Variations and modifications to those preferred embodiments will be readily apparent to persons skilled in the art of DCB crack growth sensors. All such variations and modifications are intended to be encompassed by the claims set forth hereinafter.

We claim:

1. An apparatus for monitoring crack growth in a reactor pressure vessel or piping of a nuclear reactor, comprising:

a double-cantilever beam crack growth sensor comprising first and second cantilever beams and a crack formation zone, each of said first and second cantilever beams having one end joined to said crack formation zone; and hollow expandable means having respective ends which are mechanically coupled to the other ends of said first and second cantilever beams, said hollow expandable means being expandable only in a predetermined direction in response to fluid pressure therein, said hollow expandable means exerting a load that urges the other ends of said first and second cantilever beams mutually apart, the magnitude of said load being dependent in part on the pressure inside said hollow expandable means.

2. The crack growth monitoring apparatus as defined in claim 1, wherein said hollow expandable means is a bellows.

3. The crack growth monitoring apparatus as defined in claim 1, further comprising pressurizing means for supplying fluid having a predetermined pressure to said hollow expandable means.

4. The crack growth monitoring apparatus as defined in claim 3, wherein said respective ends of said hollow expandable means are mechanically coupled to said other ends of said first and second cantilever beams by means of first and second mounting components connectable in load transfer relationship with said other ends of said first and second cantilever beams.

5. The crack growth monitoring apparatus as defined in claim 4, wherein:

said second mounting component has a pressurization chamber formed therein;

said hollow expandable means is fixed to said second mounting component in pressure receiving relationship and is expandable in said predetermined direction in response to pressure applied by said fluid from within said pressurization chamber; and said pressurizing means is coupled in fluid transfer relationship with said pressurization chamber.

6. The crack growth monitoring apparatus as defined in claim 4, further comprising a preloading actuator mounted with said first mounting component, said preloading actuator having a contact surface opposing said hollow expandable means and actuatable to move parallel to and opposite to said predetermined direction, and a force transfer component intermediate said contact surface and said hollow expandable means for transferring a preloading force from said preloading actuator to said hollow expandable means.

7. The crack growth monitoring apparatus as defined in claim 6, further comprising load cell means having an electrical output and being operatively coupled with said hollow expandable means and said first mounting component for sensing an amount of force being exerted on said first mounting component by said hollow expandable means.

8. The crack growth monitoring apparatus as defined in claim 6, wherein said force transfer component is spherically shaped and made of electrically insulative material, and said preloading actuator is a set screw threadably engaged within said first mounting component.

9. The crack growth monitoring apparatus as defined in claim 2, wherein said bellows has a spring constant of not less than about 200 lbs/inch.

10. The crack growth monitoring apparatus as defined in claim 2, further comprising a mandrel coupled to one end of said bellows and extending substantially thereinto.

11. The crack growth monitoring apparatus as defined in claim 1, wherein said fluid is an inert gas.

12. The crack growth monitoring apparatus as defined in claim 2, further comprising displacement sensor means operatively coupled to said first and second spaced beam components for deriving signals corresponding to a mutual displacement of said beam components at a selected location.

13. The crack growth monitoring apparatus as defined in claim 12, wherein said displacement sensor means comprises:

a first sensor component magnetized to form a magnetic field, mounted upon and movable with said first beam component;

a second sensor component mounted upon said second beam component at a location within said magnetic field, spaced a given distance from said first sensor component and having a field-induced output corresponding to said given distance; and means responsive to said output for deriving mutual displacement of said spaced beam components at said selected location.

14. The crack growth monitoring apparatus as defined in claim 12, wherein said displacement sensor means comprises:

a core component formed of ferromagnetic material coupled with said bellows and movable therewith;

a stationary sensing coil component surrounding said core component and electrically energizable to have an output signal;

means for electrically energizing said stationary coil component; and means responsive to said output signal for deriving a displacement signal corresponding with the spacing between said spaced beam components at said selected location.

15. The crack growth monitoring apparatus as defined in claim 12, wherein said displacement sensor means comprises:

first and second capacitor defining assemblies mounted at select locations along said first and second beam components and each including a first capacitor component mounted upon said first beam component and a second capacitor component mounted upon said second beam component and spaced from said first capacitor component to define a capacitor; and circuit means electrically coupled with each of said first and second capacitor components for coupling them as a capacitor within a circuit having an output corresponding to the capacitance exhibited thereby.

16. The crack growth monitoring apparatus as defined in claim 12, wherein said displacement sensor means comprises:

laser beam reflection means mounted upon and movable with said first beam component;

a laser beam source mounted upon and movable with said second beam component and directed toward said laser beam reflection means;

means for detecting impingement thereon of a laser beam, said detecting means being mounted upon and movable with said second beam component; and means for determining the time for a laser beam to travel from said laser beam source to said detecting means by way of said laser beam reflection means.

17. A method for applying a crack growth-inducing load to a test specimen having a pre-formed crack intermediate first and second spaced beam components extending from the crack to a mouth located at the first and second ends of the beams, comprising the steps of:
applying for a first period of time a first predetermined load in a predetermined direction such that said first predetermined load urges said first and second spaced beam components in opposite directions; and
applying for a second period of time a second predetermined load in said predetermined direction such that said second predetermined load urges said first and second spaced beam components in opposite directions,
wherein said second predetermined load is not equal to said first predetermined load, said first predetermined load being produced by the summed force of a first predetermined spring load and a first predetermined fluid pressure and said second predetermined load being produced by the summed force of a second predetermined spring load and a second predetermined fluid pressure, said spring load being a function of the distance separating said first and second spaced beam components.

18. The method as defined in claim 17, wherein said first and second predetermined loads are produced by installing a bellows between said first and second spaced beam components and supplying pressurized fluid having first and second predetermined pressures respectively to said bellows.

19. The method as defined in claim 18, further comprising the steps of:
measuring the distance separating said first and second spaced beam components at a first time before application of said first predetermined load and at a second time after application of said first predetermined load and before application of said second predetermined load; and
selecting said second predetermined load to compensate for any change in the spring load exerted by said bellows caused by a change in said measured distance.

20. An apparatus for monitoring crack growth in a reactor pressure vessel or piping of a nuclear reactor, comprising:
a double-cantilever beam crack growth sensor comprising first and second cantilever beams and a crack formation zone, each of said first and second cantilever beams having one end joined to said crack formation zone;
hollow expandable means having a spring constant and having respective ends which are mechanically coupled to the other ends of said first and second cantilever beams, said hollow expandable means being expandable in a predetermined direction only in response to fluid pressure therein, said hollow expandable means exerting a load that urges the other ends of said first and second cantilever beams mutually apart, the magnitude of said load being dependent on the pressure inside said hollow expandable means and the spring constant of said hollow expandable means; and
displacement sensor means operatively coupled to said first and second spaced beam components for deriving signals corresponding to a mutual displacement of said beam components at a selected location.

* * * * *